(12) United States Patent
Sanderson et al.

(10) Patent No.: US 10,932,714 B2
(45) Date of Patent: Mar. 2, 2021

(54) FREQUENCY ANALYSIS FEEDBACK SYSTEMS AND METHODS

(71) Applicant: Soniphi LLC, Incline Village, NV (US)

(72) Inventors: Matthew Sanderson, Incline Village, NV (US); Mark Hinds, Incline Village, NV (US)

(73) Assignee: Soniphi LLC, Incline Village, NV (US)

( * ) Notice: Subject to any disclaimer, the term of this patent is extended or adjusted under 35 U.S.C. 154(b) by 137 days.

(21) Appl. No.: 15/411,633

(22) Filed: Jan. 20, 2017

(65) Prior Publication Data

US 2017/0202509 A1 Jul. 20, 2017

Related U.S. Application Data

(60) Provisional application No. 62/281,076, filed on Jan. 20, 2016.

(51) Int. Cl.
```
A61B 5/00      (2006.01)
A61M 21/02     (2006.01)
A61M 21/00     (2006.01)
A61B 7/00      (2006.01)
A61H 1/00      (2006.01)
```
(Continued)

(52) U.S. Cl.
CPC ............ *A61B 5/4803* (2013.01); *A61B 5/486* (2013.01); *A61B 5/4836* (2013.01); *A61B 7/00* (2013.01); *A61H 1/008* (2013.01); *A61H 23/02* (2013.01); *A61M 21/02* (2013.01); *A61N 5/06* (2013.01); *A61B 5/726* (2013.01); *A61B 5/7246* (2013.01); *A61B 2562/0204* (2013.01); *A61H 2201/10* (2013.01); *A61H 2201/501* (2013.01); *A61H 2201/5092* (2013.01); *A61H 2230/00* (2013.01); *A61H 2230/105* (2013.01); *A61H 2230/505* (2013.01); *A61H 2230/655* (2013.01); *A61M 2021/0022* (2013.01); *A61M 2021/0027* (2013.01); *A61M 2021/0044* (2013.01);
(Continued)

(58) Field of Classification Search
CPC ............... A61B 5/486; A61B 5/4836; A61M 2021/0005; A61M 2021/0022; A61M 2021/0027; A61M 2021/0044
See application file for complete search history.

(56) References Cited

U.S. PATENT DOCUMENTS 6,463,327 B1 * 10/2002 Lurie ................ A61H 31/00
                                                           607/42
7,520,861 B2   4/2009 Murphy
(Continued)

FOREIGN PATENT DOCUMENTS

WO     2010039465 A2    4/2010
WO     2014037937 A2    3/2014
(Continued)

*Primary Examiner* — Carrie R Dorna
(74) *Attorney, Agent, or Firm* — Fish IP Law, LLP

(57) ABSTRACT

A health status modulator analyzes frequencies emitted by a person to select and implement improvement frequencies at the person. The health status modulator detects frequency information generated at the person, for example a voice sample or a vibrational frequency, and determines which significant frequencies exist within that sample. The modulator could then seek to modify the person's state my implementing alternative frequencies that reinforce detected ideal frequencies, introduce missing ideal frequencies, or counter and eliminate negative frequencies.

20 Claims, 3 Drawing Sheets

(51) Int. Cl.
*A61H 23/02* (2006.01)
*A61N 5/06* (2006.01)
*A61N 1/04* (2006.01)
*A61N 1/36* (2006.01)
*A61N 2/00* (2006.01)
*A61N 5/067* (2006.01)

(52) U.S. Cl.
CPC ..... *A61M 2205/50* (2013.01); *A61M 2230/06* (2013.01); *A61M 2230/10* (2013.01); *A61M 2230/50* (2013.01); *A61M 2230/65* (2013.01); *A61N 1/0456* (2013.01); *A61N 1/36014* (2013.01); *A61N 2/00* (2013.01); *A61N 2005/067* (2013.01)

(56) References Cited

U.S. PATENT DOCUMENTS 8,078,470 B2 12/2011 Levanon et al.
2004/0254501 A1* 12/2004 Mault .................... A61B 5/486 600/587
2005/0043644 A1* 2/2005 Stahmann ............ A61B 5/0031 600/529
2005/0085865 A1 4/2005 Tehrani
2015/0234886 A1 8/2015 Levanon
2016/0095545 A1 4/2016 Levanon
2016/0196837 A1 7/2016 Levanon
2017/0133035 A1* 5/2017 Jeon ....................... A61M 21/02
2017/0143246 A1* 5/2017 Flickinger ............ A61B 5/6826

FOREIGN PATENT DOCUMENTS

| WO | 2014037937 A3 | 3/2014 |
| WO | 2014188408 A1 | 11/2014 |
| WO | 2015019345 A1 | 2/2015 |
| WO | 2015187732 A1 | 12/2015 |
| WO | 2016035069 A1 | 3/2016 |
| WO | 2016035070 A2 | 3/2016 |
| WO | 2016035070 A3 | 3/2016 |
| WO | 2016185460 A1 | 11/2016 |

* cited by examiner

FREQUENCY ANALYSIS FEEDBACK SYSTEMS AND METHODS

This application claims the benefit of priority to U.S. Patent Provisional Application No. 62/281,076 filed on Jan. 20, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is wavelet analysis of vocal samples.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Automatically diagnosing the state of a living entity using electronic devices is difficult without bulky machinery, for example an x-ray machine or an ultrasound machine. While portable diagnosis machinery exists, such machinery is typically quite expensive as it requires specialized hardware, such as a radiation emitter or an ultrasound emitter and a sonograph.

For example, U.S. Pat. No. 7,520,861 to Murphy teaches a lung sound diagnostic system that collects, organizes, and analyzes lung sounds associated with inspiration and expiration of a patient. Murphy's system uses transducers that are placed at various sites around the patient's chest, which are coupled to signal processing circuitry that digitizes the data and transmits the data to a computer station. Murphy's system, requires expensive, specialized hardware in an environment that needs a great deal of advance notice to set up. Murphy's system also merely diagnoses the state of the patient and fails to provide any sort of treatment.

U.S. Pat. No. 8,078,470 to Levanon teaches a system that analyzes intonation of a speaker to determine the emotional attitude of the speaker. Levanon's emotional attitude system records and digitizes a word spoken by the speaker, and processes the digital signal to determine the average frequency of the speaker, and compares that average frequency to reference frequencies to determine the speaker's emotional state. Levanon's emotional attitude system is easy to set up with commonly available computer devices since it only requires a voice recorder and a computer. Levanon's emotional attitude system, however, only identifies the speaker's emotional state, and fails to provide any way to alter the speaker's state in any manner.

US WO 2014/188408 to Levanon teaches a diagnosis system that detects a multisystem failure in a patient by analyzing the patient's speech. Levanon's diagnosis system calculates an intensity of the patient's speech across a plurality of frequencies, and determines whether the patient is suffering from a multisystem failure by the number of vibrations found in a portion of the patient's speech. Levanon's diagnosis system may be used to detect a patient's multisystem failure, but fails to provide any way to alter the patient's state in any manner.

Thus, there is still a need for systems and methods to diagnose the state of a living entity and alter the state using commonly available hardware.

SUMMARY OF THE INVENTION

The inventive subject matter provides apparatus, systems, and methods in which a health status modulator analyzes frequencies emitted by a person to select and implement improvement frequencies at the person. The system could use any suitable frequency information to derive the health of the person, for example bio-acoustic information, bio-electronic information (e.g. electromagnetic frequencies, heart-rate frequencies, galvantic skin response frequencies), bio-magnetic information, bio-vibrational information, and bio-luminescent information (light frequencies). As used herein, "bio-acoustic information" comprises sonic information embedded within a voice sample—excluding linguistic data. As used herein, "linguistic data" comprises any information that requires knowledge of a language to decipher and/or understand, such as English, Russian, or Mandarin Chinese. As used herein, "bio-electronic information" comprises electronic impulses, such as current, voltage, and frequency, emanating from a person. As used herein, "bio-magnetic information" comprises any magnetic fields detected from a person. As used herein, "bio-vibrational information" comprises any tactile vibrations detected upon a surface of a person or upon a surface of clothing worn by the person. As used herein, "bio-luminescent information" comprises light waves reflecting off of a surface of the person. Preferably, the system uses the frequency information to develop a protocol that implements a frequency for a duration of time at the person. As used herein, "at the person" means within two meter's distance from a center of the person, and more preferably within 1.5 meter's distance from a center of the person, within 1 meter's distance from a center of the person, or even within 0.5 meter's distance from the center of the person.

Devices located "at the person" could be worn by the person, be placed within a pocket worn by the person, could be embedded within a body part of the person, or could be placed within a proximate area of the person. Any suitable computer system device could be used, for example a desktop computer system or a mobile computer system (e.g. laptop, mobile phone). An application could be installed on any computer system having a frequency sensor to enable that computer system to collect frequency information from the person.

The system can collect frequency information from the person in a variety of ways. In some embodiments, the system collects passive emitted frequency data, such as bio-acoustic information via a person speaking into a microphone or heart rate information via a person wearing an electro dermal device. In systems that collect bio-acoustic information, the system could record one or more voice samples that contain bio-acoustic information emitted by the person's voice. The system could collect one or more voice samples actively, for example in response to the person activating a trigger via a user interface, or could collect the voice sample passively by monitoring sounds emitted by the person. In some embodiments, the system could be initialized to recognize the person's voice via a speech recognition algorithm. Once the system has been initialized, the system could analyze sounds and filter out ambient noise that is not recognized as originating from the person. In some embodiments, the system is programmed to collect mel-frequency cepstrum coefficients (MFCC) from the bio-acoustic information on a mel scale.

In other embodiments the system emits frequencies at the person, such as a laser aimed at portions of the person's body at a frequency or an electrode that transmits electronic signals through the person's body, and detects frequency feedback from the person's body similar to a radar "pinging" portions of the person's body. In systems that collect bio-electronic information, the system could record electronic impulses detected through an electrodermal sensor. In some embodiments, the system implements a frequency sweep of a part of the person's body to derive the strength of resonant frequencies.

Frequency information could be collected by a sensor at the person, for example a microphone embedded in a cellular phone or an electronic wearable device functionally coupled to a computer system, which transmits frequencies to a centralized computer system for analysis. In some embodiments, the sensor could be surgically implanted within the person's body, such as within a pacemaker or other implantable device, which transmits detected frequencies to a computer system functionally coupled to the sensor. As used herein, an electronic device that is "functionally coupled" to another electronic device is coupled in such a way as to allow electronic data to be transmitted from one electronic device to another electronic device, using a wired or wireless data connection. Contemplated sensors include microphones, electroencephalograms, electrodermal sensors, cameras, infrared sensors, and antennas. The frequency information could be a sample over any period of time suitable to collect enough information to derive a set of frequency data, for example at most 2 seconds, at most 5 seconds, at most 10 seconds, at most 30 seconds, at most 1 minute, or even at most 5 minutes. In some embodiments, a user interface might be presented to the person, triggering the person to perform an activity that would cause frequencies of the person to be easier to capture, such as placing electrodermal sensors on a portion of the person's body, or read a sentence presented on the user interface into a microphone sensor. The sensor could be configured to transmit either the raw data to a remote computer system, or could be configured to transmit only derived frequency information (e.g. bio-acoustic information, bio-electronic information, bio-magnetic information, bio-vibrational information, or bio-luminescent information) to a remote computer system distal from the person for processing.

Frequency information extracted from the collected raw sensor data is typically transmitted to a frequency processing module to be analyzed. In preferred embodiments, the frequency information is analyzed by a computerized frequency processing module which derives frequency information from the collected raw data from the sensor or sensors at the person. Preferably, a full spectral analysis of the raw data is performed in order to extract as much frequency information as possible from the raw data. Exemplary frequency information includes, for example, a highest dB (decibel) reading, a lowest dB reading, cumulative octave readings, harmonics, and logical groupings of frequencies. In some embodiments, the frequency processing module could be configured to derive one or more significant frequencies from the raw data. As used herein, a "significant frequency" comprises a recurring (more than 5 times) frequency that can be detected in at least 80% of a contiguous portion of the received frequency information.

Once one or more "significant frequencies" are identified, the significant frequencies could be fed to a frequency analysis module, which compares the significant frequencies against a library of frequencies that relate to emotions (happy, sad, angry, stressed), health status, and physiology (toxicity, nutrient level, hormonal imbalances). The library of frequencies can be pulled from any suitable source, for example a communal library (shared by all users of the system), a master library (created by administrators of the system), or a personal library (created by a user or subset of users of the system). Personal libraries could be created and maintained by a user or a subset of users who record frequencies when the user has an emotional state, a physiological condition, or a health status. The system could then record and save significant frequencies detected during that recording and store that significant frequency in the library to identify when the user (or set of users) is emitting that significant frequency, which reflects that state.

The frequency library could be tagged with positive and negative significant frequencies, which and could be weighted in accordance with any suitable algorithm, for example an automated template that chooses optimal frequencies for selected user types (e.g. an athlete user type may have a first set of weighted significant positive/frequencies while an accountant user type may have a different set of weighted significant positive/frequencies). The system could then identify which of the detected significant frequencies are weighted the most, and implement a protocol to alter a state of the person. For example, the system could reinforce an existing significant positive frequency, introduce a missing significant positive frequency that is over a threshold weight, or could cancel an existing negative frequency. The system is programmed to address the highest weighted frequencies (or lowest weighted frequencies, in the case of a negative weight for negative frequencies) when reinforcing, introducing, or canceling a significant frequency.

Typically analysis module develops the protocol as a function of a portion of the frequency information. As used herein, a protocol that "implements" a frequency at a duration is one that instructs a device to resonate at the frequency for the duration specified. A protocol could be configured to implement a plurality of frequencies at a plurality of durations if need be. Such frequencies could be implemented using any suitable device that could be directed to resonate at a frequency, for example an audio speaker, a laser, a light source, a pulsed electromagnetic field (PEMF) device, a SCALAR wave device, a transcutaneous electrical nerve stimulation (TENS) device, a microcurrent electrical nerve stimulation (MENS) device, or a vibrational motor that transmits a tactilely sensible vibrational frequency. In some embodiments, the system could construct a protocol to implement a weakly detected frequency in the bio-acoustic information. In simple embodiments, the system could construct a protocol to implement the significant frequency for the period of time that the voice sample was recorded. The system could also construct a protocol to implement a harmonic of the significant frequency, multiple harmonics of the significant frequency, or could implement the significant frequency via different modalities (e.g. via an audio sound and also a visual light). In some embodiments, the protocol could implement the frequency by aiming the frequency at a portion of the person's body, for example the person's ears, eyes, nose, throat, chest, or hips. In other embodiments, the protocol could implement the frequency by aiming the frequency at multiple portions of the person's body, and could implement different frequencies at different portions of the person's body (e.g. directing the significant frequency towards the person's ears, and a harmonic of the significant frequency towards the person's diaphragm). Where a plurality of frequencies are directed at a person, each frequency could be implemented at a different duration and/or duty cycle.

The system could receive several sets of frequency information from a person, for example through several samples of data collected from the sensors one after another (e.g. within 5 minutes of one another) or through several historical samples of data submitted over time and saved to an archived database (e.g. one week, one month, or even one year after one another). Several protocols could be developed, one for each set of frequency information, and/or each type of frequency information. In some embodiments, the system could be configured to compare a first set of frequency information with a second set of frequency information in order to develop a follow-up protocol. For example, where the system is configured to strengthen a significant frequency of a person, the system could detect a decibel level of the person's significant frequency in accordance with the first set of frequency information, and the decibel level of the person's significant frequency in accordance with the second set of frequency information, and could increase/decrease the intensity of the implemented frequency depending upon if the significant frequency decreased/increased in decibel level, respectively. In some embodiments, the system could be configured to save the received frequency information to a database to provide a historical frequency map of the person. Such historical frequency maps could be used to develop person-specific protocols.

For example, the system could determine that the person regains an intensity in voice samples or frequency feedback when a first frequency is implemented at the person, but fails to regain an intensity (or does not gain as large an intensity) when a second frequency is implemented at the person. The system could then favor implementing the first frequency at the person when such an analysis is performed. In some embodiments, the system could save the raw frequency information into the database, but preferably the system only saves historical analysis information to the database to save space. Exemplary analysis information includes a significant frequency of the person, a set of harmonic frequencies that are known to strengthen the significant frequency of the person, the highest recorded decibel frequency, the lowest recorded frequency, the types of frequency recorded and implemented at the person, and a preferred significant frequency of the person. The system could save the frequency information in a variety of ways, for example by molecular weight and frequency correlations, by genetic code and wavelength correlations, and/or as light emission spectral analysis data.

Once one or more protocols have been developed by the analysis module, the system could feed the protocol to a computerized effector transmitter that transmits the treatment frequency to a frequency implementer for a corresponding duration at the person. Contemplated frequency implementers include any device that can implement a frequency, such as an audio speaker, a light source (e.g. an LED or laser), a vibrational source, a microcurrent emitter, a PEMF device, and a SCALAR wave device. In some embodiments, the frequency implementer modifies the frequency of an environment about the person, such as a home entertainment system or a car entertainment system, and in other embodiments the frequency implementer modifies the frequency by coupling to the person, for example via headphones, a bracelet, or a head-band, and emits frequencies in any modality—even through bone conductions that deliver frequency through one or more organs of the body (e.g. jawbone to ear canal). In preferred embodiments, a laser or other aiming device could be used for extreme targeting of a person or a portion of a person's body. Both targeted bands and untargeted bands could be used. The frequencies could be implemented in a single phase, biphasic, or in multiple phases, and alternating frequencies could be implemented (e.g. a first frequency then a second frequency and then the first frequency again, or a first, second, then third frequency followed by the first frequency again). Such frequency implementers could implement the protocol at the person in order to affect the health status of the person, for example by reinforcing, introducing, or cancelling a frequency.

Various objects, features, aspects and advantages of the inventive subject matter will become more apparent from the following detailed description of preferred embodiments, along with the accompanying drawing figures in which like numerals represent like components. For example, instead of implementing frequencies at the person, the system could be configured to implement the frequency into food or water, which could then be ingested by the person. In other embodiments, the system could be configured to implement the frequency into an ingestible medium or into a wearable medium (e.g. a quartz crystal), which is then transported to the person for wearing.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
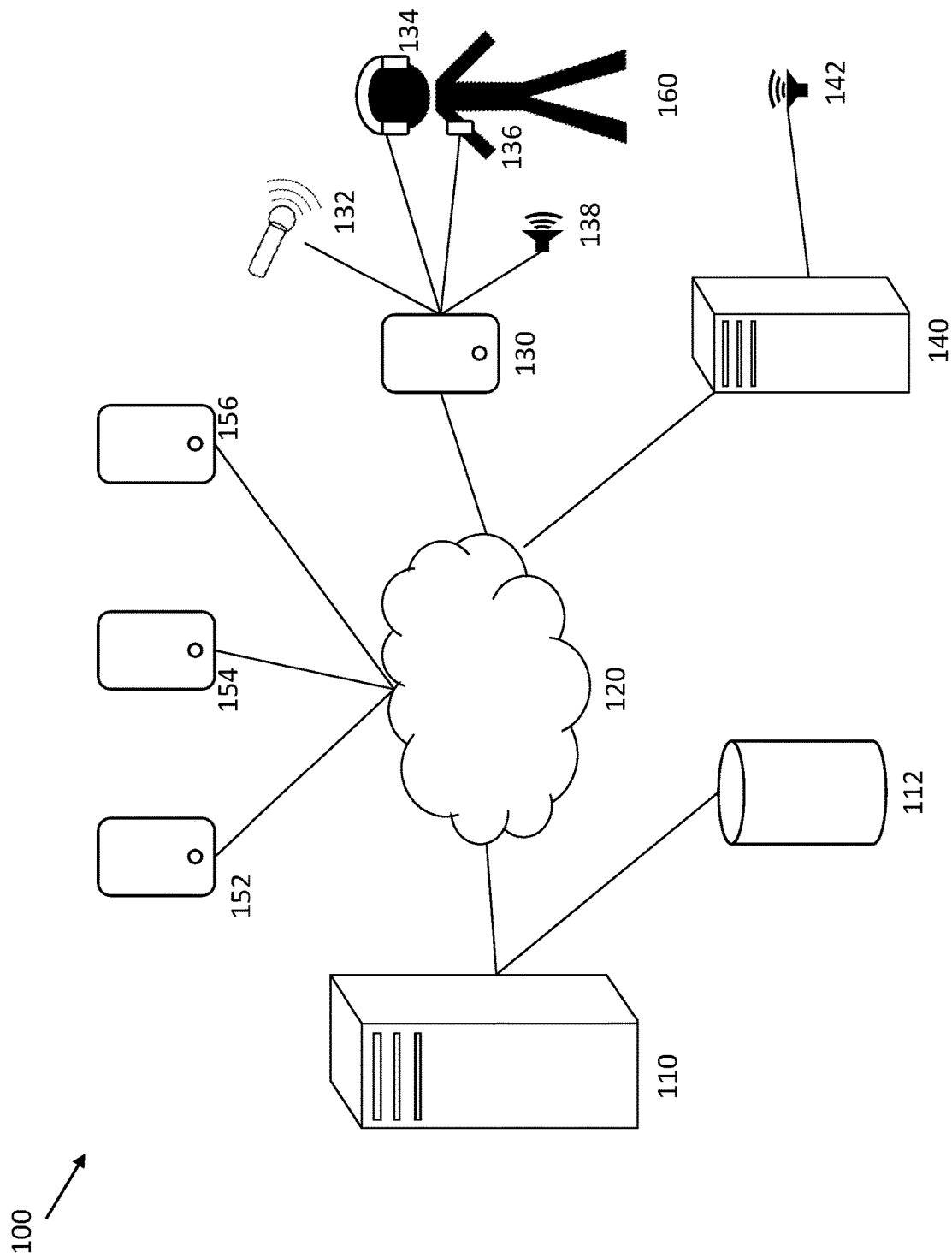
FIG. 1 is an exemplary system distributed on a computer system and a portable device at the person

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. One should appreciate that the systems disclosed herein can be used to detect one or more significant frequencies at a person and reinforce existing significant frequencies, introduce missing significant frequencies, and/or cancel existing significant frequencies.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In FIG. 1, a system 100 includes an analysis computer system 110, a network 120, a control computer system 130, control computer system 140, control computer system 152, control computer system 154, control computer system 156, and a person 160.

Analysis computer system 110 is shown euphemistically as a single computer tower having a processor and a non-transient memory with software configured to perform analysis and protocol development on a voice sample or a set of frequency information, but analysis computer system 110 could be distributed among a plurality of computers, or could be implemented on a network cloud without departing from the scope of the current invention. Data repository 112 is functionally coupled to computer system 110 and stores data collected and/or analyzed by analysis computer system 110, such as frequency data, health status reports, profile data for one or more users of the system, and/or preferences. Such data sources typically store collected information in a text file, such as a log, csv, JSON or an XML file. Data repository 112 could be a database management system ("DBMS"), which keeps data in a structured environment, and typically keeps metadata log files on its datasets. While data repository 112 is shown euphemistically as a single data repository, any number of data sources and any type of data source could be used without departing from the scope of the invention. The data sources coupled to computer 110 could number in the hundreds or even thousands, to provide a large corpus of datasets that may or may not be known to computer system 110, where many of the data sources might use different types of data structures. Both analysis computer system 110 and data repository 112 could be distributed systems in a cloud computer environment. Data repository 112 could also be considered a data source having one or more datasets that analysis computer system 110 could draw upon. Data repository 112 could also contain a historical log that tracks all retrieving, profiling, querying and conforming of datasets, attributes of datasets, and associated user entity interactions to enable the system to learn from itself by analyzing trends found in the historical log.

Network 120 could be any network link that is used to communicate data from one computer system to another computer system, such as a packet-switched network, the Internet, LAN, WAN, VPN, or other suitable network system. Analysis computer system 110 communicates with various control communication systems via network 120 to transmit frequency information and frequency implementation protocols between the various devices.

Control computer systems 130, 152, 154, and 156 are shown euphemistically as mobile devices, but could be any computer system programmed to collect frequency information from one or more users, for example a wearable computer device (e.g. a badge, a pin, a button, a cufflink, a watch, a bracelet, a necklace, an elbow pad, or a piece of clothing), an implantable device, or could be coupled to a portion of a skin of person 140, such as a bracelet, a belt, or an electrodermal heart rate monitor. Control system 130 is functionally coupled to devices 132, 134, 136, and 138, which function to collect frequency information from person 160 and/or implement frequencies at person 160. For example, device 132 is shown as a microphone that collects audio frequency information, device 134 is shown as a headset that could collect vibrational frequency from person 160 and deliver vibrational frequency and/or audio frequencies at person 160, device 136 is shown as a wristband that could implement vibrational or electrical frequencies at person 160, and speaker 138 is shown as a speaker that could implement audio frequencies at person 160. Any device suitable for collecting frequency information or for delivering frequency information in any modality is contemplated. Contemplated modalities include, for example, audio modalities, light modalities, vibrational modalities, magnetic modalities, SCALAR modalities, electrical modalities, and radio frequency modalities. While control computer system 130 could be physically coupled to each device 132, 134, 136, and 138, control computer system 130 could be functionally coupled to each device through wireless means as well.

Contemplated frequency data collectors include any suitable device that could be used to collect frequency information from person 160, for example an electrodermal sensor, electroencephalogram, camera, infrared sensor, or antenna. As used herein, a "frequency dataset" is a dataset that contains oscillating wave data collected by a sensor.

One or more sensors could be implanted within person 160, but is preferably wearable, placed in a pocket, or is coupled to a portion of person 160's skin, such as a bracelet or a belt. In some embodiments, the frequency data collectors collect frequency information passively, for example by constantly collecting audio and vibrational samples from person 160, but in preferred embodiments the frequency data collectors collect frequency information in response to some sort of trigger, for example a trigger word uttered by person 160 or a button activated on control system 130. In some embodiments, control computer system 130 could transform the raw collected frequency datasets into a subset of frequency information, for example by gleaning only bioacoustic data from a voice sample and transmitting only the bioacoustic data to analysis computer system 110. However in other embodiments control computer system 130 could be configured to transmit raw frequency datasets to analysis computer system 110.

Frequency information could also include wavelets. In signal processing a wavelet is an oscillation that begins and ends at zero amplitude, with an initial increase, a peak then decreasing until its amplitude is zero. A wavelet is created using a wavelet transform which is similar to other transforms that can transform a signal from the time domain into the frequency domain, the wavelet transform however contains both the information of the time domain and the frequency domain with the Heisenberg uncertainty principle effecting its accuracy at various ranges. The wavelet can be used in signal processing to identify when a certain frequency is present in time with regards to a signal of duration N.

In the application of signal processing of discreet vocal data, the creation of distinct wavelets of single frequencies can be convolved with sample signals of the human voice to ascertain information that would show correlation between the created wavelets and the sample signal. These correlations can be of value as biometric information specific to the unique vocal print of the person whose sample was used to generate the signal.

Analysis computer system 110 could use wavelet analysis to identify unique spectral data present in the human voice as well as background noise present in a sample recorded signal obtained from a mobile device or stationary microphone. Analysis computer system 110 could convolve wavelets created at distinct frequencies with unknown sample signals to find correlations between the wavelet and the unknown signal. Through these wavelet correlations, the present invention can determine biometric data about the person whose voice was sampled, including but not limited to; bio-specific identifiers, possible biochemical presence, phase information, harmonic resonance, dissonance, and coherence of the vocal signal. When the results of these correlations are compared to the many databases that represent the bulk of the present invention's intellectual property, very specific correlations to a person's unique vocal profile can be garnered, and a general picture of the person's personality and health and wellness can be achieved.

An audio sensor is preferably configured to collect audio information from the person, such as a microphone coupled to a computer system that collects snippets of audio data, such as a 30 second, 60 second, 5 minute, or even hour long sample. Preferably, the system analyzes frequency data in the audio data and identifies quantifiable, correlative trends. For example, the system could identify correlations within the frequency data (e.g. a significant frequency or a highest increase in frequency and a highest decrease in frequency), correlations between wavelets in the audio sample (e.g. correlations between fundamental frequencies or harmonics), correlations between wavelets between audio samples, or even correlations between attributes of a wavelet and health status of that person (e.g. how wavelet attributes correlate with a disease state, a state of mind, and how those attributes change when wavelet attributes change). Such correlations could be saved to database 112 and used to determine information about the person in the future, for example the system could analyze a person's wavelet information and determine the health status of that person, or could analyze a person's wavelet information and identify the person via a saved wavelet "fingerprint" in the database.

Frequency implementers include any suitable device that could be used to implement a frequency at person 160, for example a laser, a light source, a pulsed electromagnetic field (PEMF) device, a SCALAR wave device, a transcutaneous electrical nerve stimulation (TENS) device, a microcurrent electrical nerve stimulation (MENS) device, or a vibrational motor that transmits a tactilely sensible vibrational frequency. Frequency implementers are configured to receive a frequency protocol and implement one or more frequencies at person 160 in accordance with the frequency protocol (e.g. a first frequency for a first time period, followed by as second frequency for a second time period, and so on and so forth). Multiple frequencies could be implemented at person 160 simultaneously, and the frequency data collectors could collect frequency data during implementation, transmitting that frequency data to analysis computer system 110 so that it can alter or fix the implemented protocol as needed. For example, where a first frequency is introduced to person 160, and person 160 fails to provide frequencies that reflect that frequency, computer system 110 could introduce a protocol that increases the intensity of that frequency, introduces a harmonic of that frequency, or stop introducing that frequency and provide an alternative frequency (e.g. a frequency associated with joy at a higher weight is introduced, but was not detected in subsequent frequencies collected from person 160 within a threshold period of time, so a frequency associated with relaxation at a lower weight is introduced).

Control computer systems 152, 154, and 156 are shown as other control computer systems that collect frequency information and/or implement frequencies at other persons (not shown). Control computer systems 152, 154, and 156 are shown as mobile phones, but could be any other computer system capable of collecting frequency information and/or implementing frequencies.

Analysis computer system 110 or any of the control computer systems 130, 152, 154, or 156, could be programmed to derive significant frequencies from the collected frequency information. In embodiments where the control computer systems be programmed to derive significant frequencies, only the significant frequency information could be transmitted to analysis computer system 110. In preferred embodiments, the frequency information is analyzed by a computerized frequency processing module which derives frequency information from the frequency dataset(s). Preferably, a full spectral analysis of the frequency dataset(s) is performed in order to extract as much non-linguistic frequency information as possible. Exemplary significant frequency information includes, for example, a highest dB (decibel) reading, a lowest dB reading, cumulative octave readings, harmonics, logical groupings of frequencies, and statistically significant frequencies as compared to other detected frequencies in the frequency information. In other embodiments, the frequency processing module could derive the significant frequency to be the strongest frequency detected within a portion of the frequency feedback sample, or the strongest whole-number frequency detected within a portion of the frequency feedback sample.

Figure 2:
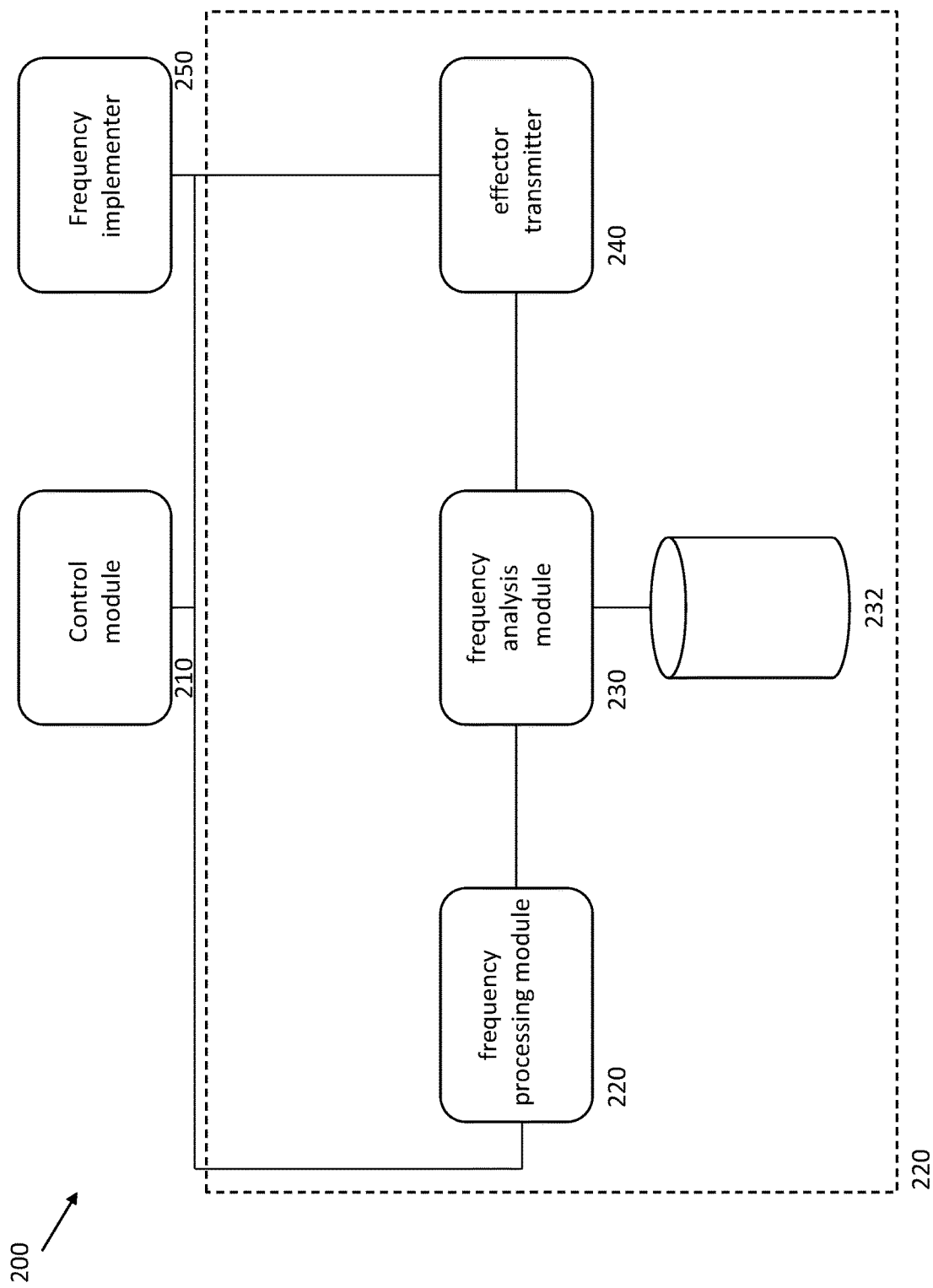
FIG. 2 is a software schematic of an exemplary computer system.

FIG. 2 shows a software schematic of modules within an analysis computer system 220, such as analysis computer system 110. Analysis computer system 220 communicates with one or more control modules and has a frequency processing module 220, frequency analysis module 230, and an effector transmitter 240.

Frequency processing module 220 receives frequency information from one or more control modules, such as control module 210, and parses out the significant frequencies (if the control module has not done so already). The significant frequencies are then transmitted to frequency analysis module 230, which detects the health state of the person by correlating the detected significant frequencies in the frequency data with historical frequencies saved in frequency database 232. Analysis computer system 220 stores frequency data in frequency database 232 that could be utilized by analysis module 230 to make correlations. The frequency data could comprise various correlations between frequencies of modalities and health statuses, such as emotional state, health state, or physiology. Any user of the system could provide additional frequency data gleaned from his/her own self, or from other frequency data archives. Such users include a user of a control module, and administrator user, or a content aggregator.

Frequency database 232 could house several sets of frequency information from one or more persons, for example through several samples of data collected from the sensors one after another (e.g. within 5 minutes of one another) or through several historical samples of data submitted over time and saved to an archived database (e.g. one week, one month, or even one year after one another). Frequency analysis module 230 could then compare the received frequency dataset information against historical frequency dataset information from the person, or from other persons with similar characteristics. The similar characteristics could be selected through an administrator user interface. For example, a user could wish to compare the frequency feedback dataset against frequency characteristics of other users who have the same racial background, the same age and sex, and/or the same profession. In some embodiments, a user could compare his/her own frequency feedback information against a selected ideal frequency dataset.

A user of the system could provide any algorithm for selecting a suitable protocol when a correlation is detected. For example, frequency analysis module could utilize an algorithm that detects whether at least one of a set of positive significant frequencies was detected, and if none of that set were detected, implement the heaviest weighted significant frequency of the set of positive significant frequencies. In another embodiment, frequency analysis module could utilize an algorithm that detects whether at least one of a set of positive significant frequencies was detected, and if none of that set were detected, determine a difference between a detected significant frequency and an ideal significant frequency, and introduce another frequency in phase with the detected significant frequency that aggregates with the detected significant frequency to produce the ideal significant frequency. In another embodiment, the frequency analysis module could utilize an algorithm that detects whether at least one of a set of positive significant frequencies was detected, and if one of that set is detected, reinforce that significant frequency. In another embodiment, frequency analysis module could utilize an algorithm that detects whether at least one of a set of negative significant frequencies was detected, and if one of that set is detected, implement an opposing frequency at the person to cancel out the negative significant frequency. It should be apparent to those skilled in the art that many more combinations and algorithms besides those already described are possible. Maintenance algorithms could also be implemented to implement alternative protocols where a first protocol fails to prove effective (i.e. the change in the person's detected significant frequencies falls below a threshold level).

Frequency analysis module 230 chooses a protocol that implements a frequency at a corresponding duration. Typically the frequency information is fed into an effector transmitter that transmits the protocol to a frequency implementer, either directly such as a transmission to frequency emitter 250, or indirectly through a control module functionally coupled to a frequency emitter, such as control module 210. As used herein, a protocol that "implements" a frequency at a duration is one that instructs a device to resonate at the frequency for the duration specified. A protocol could implement one or more frequencies at one or more durations at one or more modalities if need be. Such frequencies could be implemented using any suitable device that could be directed to resonate at a frequency, for example an audio speaker, a laser, a light source, a pulsed electromagnetic field (PEMF) device, a SCALAR wave frequency, or a vibrational motor that transmits a tactilely sensible vibrational frequency.

The system could also construct a protocol to implement a harmonic of the significant frequency, multiple harmonics of the significant frequency, or could implement the significant frequency via different modalities (e.g. via an audio sound and also a visual light). In some embodiments, the protocol could implement the frequency by aiming the frequency at a portion of the person's body, for example the person's ears, eyes, nose, throat, chest, or hips. In other embodiments, the protocol could implement the frequency by aiming the frequency at multiple portions of the person's body, and could implement different frequencies at different portions of the person's body (e.g. directing the significant frequency towards the person's ears, and a harmonic of the significant frequency towards the person's diaphragm). Where a plurality of frequencies are directed at a person, each frequency could be implemented at a different duration, phase, and/or duty cycle.

Figure 3:
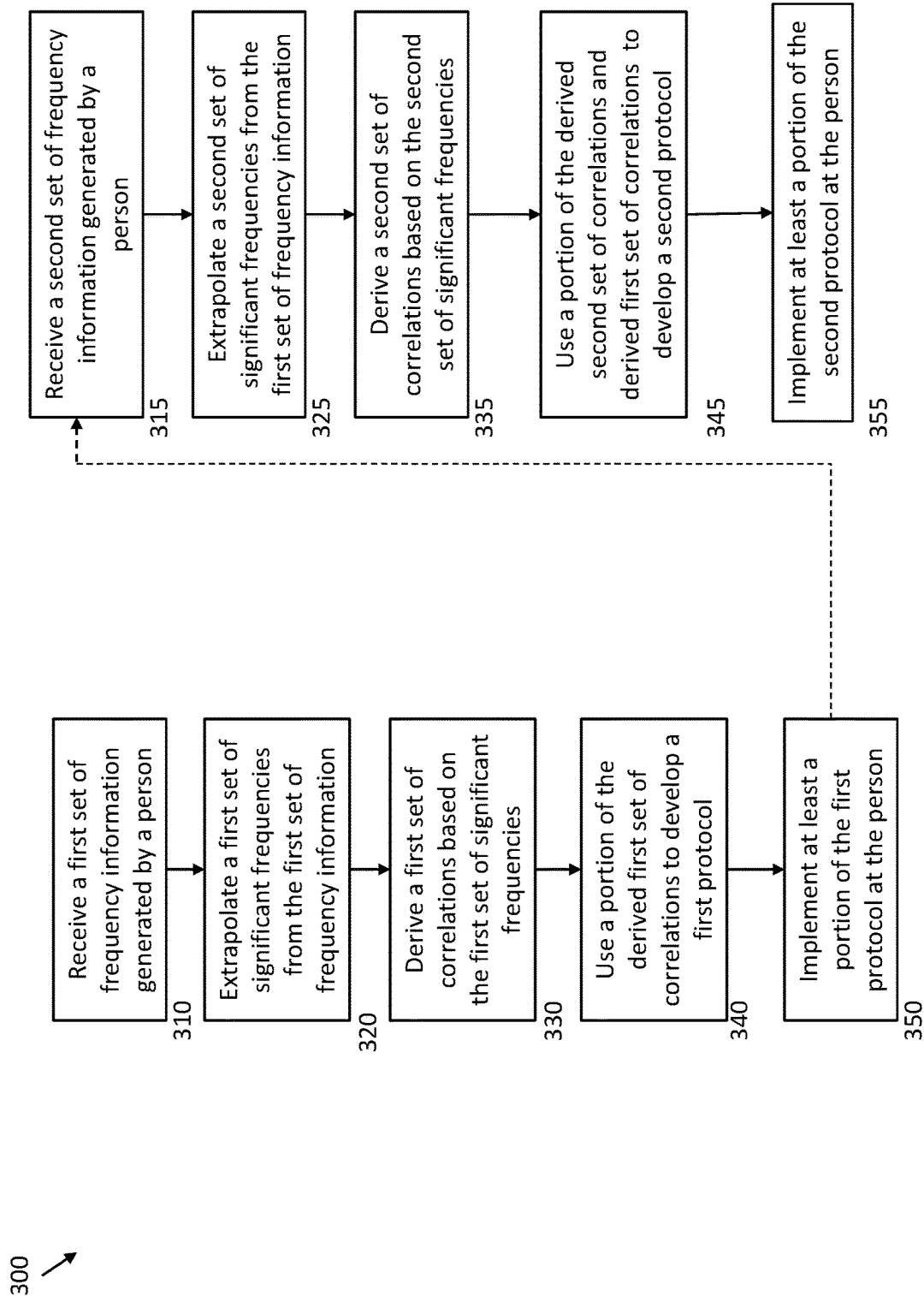
FIG. 3 is a flowchart of steps to monitor and effect the health status of a person.

FIG. 3 shows an exemplary method for analyzing detected frequencies and implementing improvement frequencies. In step 310, the system receives a first set of frequency information generated by a person from a set of frequency sensors. In step 320, the system extrapolates a first set of significant frequencies from the first set of frequency information, and derives a set of correlations based on the set of significant frequencies. As used herein, a "set" of items includes at least one item. The correlations are then used to develop a protocol in step 340, which are then implemented at the person using any suitable frequency implementer.

Preferably, a feedback loop is also implemented, such that additional frequency information is collected in step 315. Again, the system runs through similar steps of extrapolating an updated set of significant frequencies in step 325, and deriving correlations based on the significant frequencies in step 335. In step 345, the system compares the updated derived correlations against historical derived correlations to determine how effective the previous protocol was at effecting change at the person, and could then implement a second protocol as a function of those correlations. In step 355 the system then implements a the second protocol at the person using one or more frequency implementers. The feedback loop could be continued for any period of time for a user of the system.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for improving a health status of a person comprising:
   extrapolating a first set of significant frequencies from a first set of bio-acoustic information comprising sonic information embedded within the person's voice;
   deriving a first set of correlations based on the first set of significant frequencies;
   using at least a portion of the derived first set of correlations to develop a first protocol that implements a first frequency at a corresponding first duration;
   implementing at least a portion of the first protocol at the person's body;
   comparing the first set of significant frequencies against a library of frequencies having a plurality of frequencies that are related to at least one of emotion, health status, and physiology;
   tagging each of the plurality of frequencies in the library of frequencies as a positive or negative significant frequency, weighing the tagged frequencies in the library of frequencies in accordance with an algorithm; and
   identifying the first frequency in the first set of significant frequencies that is the heaviest positively weighed in the library of frequencies.

2. The method of claim 1, further comprising:
   extrapolating a second set of significant frequencies from a second set of bio-acoustic information comprising sonic information embedded within the person's voice after implementing the portion of the first protocol at the person,
   deriving a second set of correlations in the second set of frequency information;
   using at least a portion of the derived second set of correlations to develop a second protocol that implements a second frequency at a corresponding second duration; and
   implementing at least a portion of the second protocol at the person's body.

3. The method of claim 2, wherein the step of using the portion of the derived second set of correlations to develop the second protocol comprises selecting the second frequency as a function of a difference between the second set of significant frequencies and the first set of significant frequencies.

4. The method of claim 2, wherein the second frequency comprises an alternative frequency to the first frequency, when the first frequency is not detected in subsequent frequencies collected from the person within a threshold period of time.

5. The method of claim 1, further comprising receiving the first set of significant frequencies from a cellular phone.

6. The method of claim 1, further comprising receiving the first set of significant frequencies from a wearable device.

7. The method of claim 1, wherein the step of deriving the first set of correlations comprises deriving correlations within a single wavelet.

8. The method of claim 1, wherein the step of deriving the first set of correlations comprises deriving correlations between wavelets.

9. The method of claim 1, further comprising receiving a first set of health data about the person, wherein deriving the first set of correlations comprises deriving correlations between the first set of significant frequencies and the first set of health data.

10. The method of claim 9, wherein the first frequency comprises at least one of the first set of the significant frequencies.

11. The method of claim 9, wherein the first frequency comprises a harmonic of at least one of the first set of the significant frequencies.

12. The method of claim 1, wherein implementing at least a portion of the first protocol at the person's body comprises reinforcing an existing significant positive frequency.

13. The method of claim 1, wherein implementing at least a portion of the first protocol at the person's body comprises introducing a missing significant positive frequency.

14. The method of claim 1, wherein implementing at least a portion of the first protocol at the person's body comprises canceling an existing negative frequency.

15. The method of claim 1, wherein extrapolating the first set of significant frequencies comprises emitting frequencies at the person and detecting frequency feedback from the person's body.

16. A method for improving a health status of a person comprising:
   extrapolating a first set of significant frequencies from a first set of bio-acoustic information comprising sonic information embedded within the person's voice;
   deriving a first set of correlations based on the first set of significant frequencies;
   using at least a portion of the derived first set of correlations to develop a first protocol that implements a first frequency at a corresponding first duration;
   implementing at least a portion of the first protocol at the person's body;
   wherein the step of extrapolating the first set of significant frequencies from the first set of bio-acoustic information comprises identifying frequencies that appear more than five times in at least 80% of a contiguous portion of the bio-acoustic information.

17. The method of claim 16, further comprising:
   extrapolating a second set of significant frequencies from a second set of bio-acoustic information comprising sonic information embedded within the person's voice after implementing the portion of the first protocol at the person,
   deriving a second set of correlations in the second set of frequency information;

using at least a portion of the derived second set of correlations to develop a second protocol that implements a second frequency at a corresponding second duration; and implementing at least a portion of the second protocol at the person's body.

18. The method of claim 16, wherein the step of deriving the first set of correlations comprises deriving correlations within a single wavelet.

19. The method of claim 16, wherein the step of deriving the first set of correlations comprises deriving correlations between wavelets.

20. The method of claim 16, further comprising receiving a first set of health data about the person, wherein deriving the first set of correlations comprises deriving correlations between the first set of significant frequencies and the first set of health data.

* * * * *